(12) United States Patent
Tortora

(10) Patent No.: US 10,495,636 B2
(45) Date of Patent: Dec. 3, 2019

(54) SYSTEM AND METHOD FOR PATHOGEN DETECTION USING MULTIPLE-SIZED POLYMER-COATED BEADS WITHIN LYOTROPIC CHROMONIC LIQUID CRYSTALS

(71) Applicant: Pathogen Systems, Inc., Broomfield, CO (US)

(72) Inventor: Luana Tortora, Stow, OH (US)

(73) Assignee: Pathogen Systems, Inc., Broomfield, CO (US)

( * ) Notice: Subject to any disclaimer, the term of this patent is extended or adjusted under 35 U.S.C. 154(b) by 0 days.

(21) Appl. No.: 15/487,291

(22) Filed: Apr. 13, 2017

(65) Prior Publication Data

US 2017/0299583 A1 Oct. 19, 2017

Related U.S. Application Data

(60) Provisional application No. 62/322,531, filed on Apr. 14, 2016.

(51) Int. Cl.
| | |
|---|---|
| *G01N 33/543* | (2006.01) |
| *G01N 33/569* | (2006.01) |
| *G01N 21/21* | (2006.01) |
| *G01N 21/59* | (2006.01) |
| *G01N 21/03* | (2006.01) |
| *G01N 21/23* | (2006.01) |

(52) U.S. Cl.
CPC ....... *G01N 33/54366* (2013.01); *G01N 21/03* (2013.01); *G01N 21/21* (2013.01); *G01N 21/59* (2013.01); *G01N 33/54313* (2013.01); *G01N 33/54326* (2013.01); *G01N 33/54373* (2013.01); *G01N 33/54393* (2013.01); *G01N 33/56916* (2013.01); *G01N 21/23* (2013.01); *G01N 2201/0683* (2013.01); *G01N 2333/245* (2013.01)

(58) Field of Classification Search
CPC ....... G01N 33/54366; G01N 33/54373; G01N 21/21; G01N 33/54326; G01N 33/54313; G01N 21/59; G01N 33/56916; G01N 33/54393; G01N 21/03; G01N 21/23
See application file for complete search history.

(56) References Cited

U.S. PATENT DOCUMENTS

| | | | |
|---|---|---|---|
| 6,411,354 B1* | 6/2002 | Lavrentovich | C09K 19/56 349/123 |
| 2002/0052002 A1* | 5/2002 | Niehaus | G01N 33/54373 435/7.1 |
| 2005/0079486 A1* | 4/2005 | Abbott | B01J 19/0046 435/5 |
| 2011/0141431 A1* | 6/2011 | Jordan | G01N 21/21 349/199 |

* cited by examiner

*Primary Examiner* — Melanie Brown
(74) *Attorney, Agent, or Firm* — Glenn H. Lenzen; Dietze and Davis, P.C.

(57) ABSTRACT

A novel detection system and method is presented, where a two-bead receptor method is used for capturing pathogens, with one type of bead being magnetic and having a size of 3 microns or smaller, and the other type being polymeric and having a size of 3 microns or larger. The first type is used to concentrate a pathogen; the latter is used to create a detectable signal. Fast sensitive detection is achieved by collecting the optical signal created by the distortion of a homeotropically aligned chromonic azo dye in the presence of captured pathogens.

9 Claims, 5 Drawing Sheets

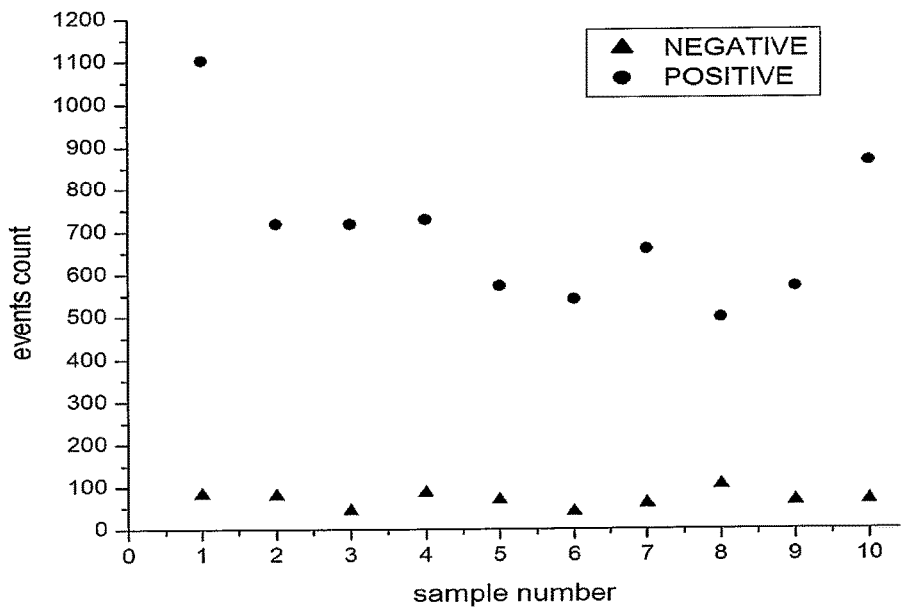
FIG. 8.A
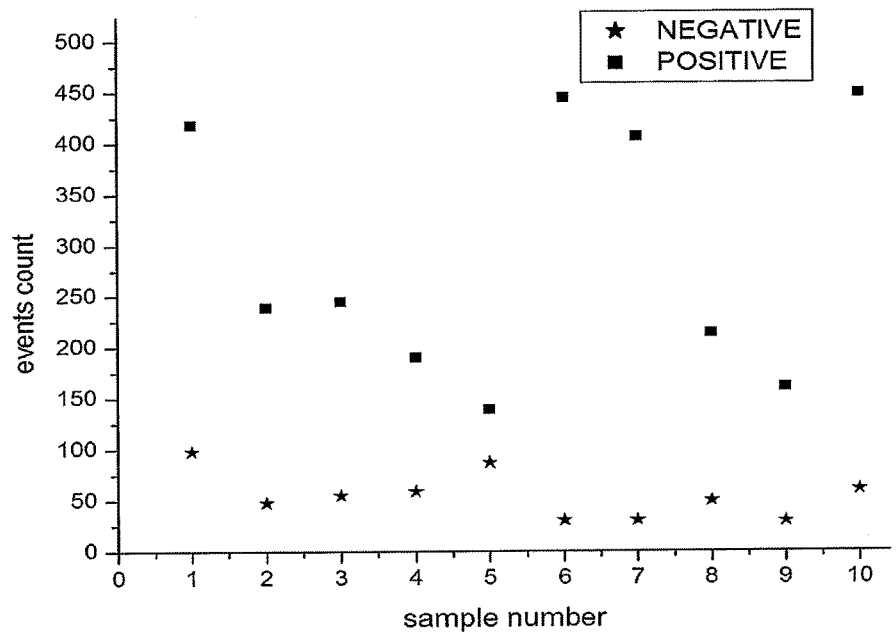
FIG. 8.B

SYSTEM AND METHOD FOR PATHOGEN DETECTION USING MULTIPLE-SIZED POLYMER-COATED BEADS WITHIN LYOTROPIC CHROMONIC LIQUID CRYSTALS

CROSS-REFERENCE TO RELATED APPLICATIONS

This application claims priority to U.S. Provisional Patent Application No. 62/322,531 filed Apr. 14, 2016, the entire disclosure of which is incorporated herein by reference.

TECHNICAL FIELD OF THE INVENTION

This invention relates to systems and methods for detecting pathogenic materials. More particularly, this invention relates to a detection technique having an amplification system employing a two-bead receptor method for capturing pathogens and a detection system incorporating a liquid crystal chromonic azo dye aligned homeotropically in a closed cell, for rapid and sensitive detection.

BACKGROUND OF THE INVENTION

Capturing bacteria by magnetic separation is a well-established technique that allows the collection of selectively concentrated pathogens for further analysis and identification. Immunomagnetic separation (IMS) technology is able to isolate bacteria strains possessing specific and characteristic surface antigens [Clinical Microbiology Reviews, 7(1), 43-54, 1994; Sensors, 9, 717-730, 2001; Critical Reviews in Microbiology, 30(1), 7-24, 2004]. Further identification of the concentrated bacteria is performed by traditional biochemical, immunologic, or molecular methods. Such technology can be used in combination with polymerase chain reaction (PCR) techniques to improve sensitivity and decrease detection time [FEMS Microbiology Letters, 176(2), 285-289, 1999; Int J Food Microbiol., 99(1), 47-57, 2005, PLoS ONE, 8(12), e82376, 2103]. Highly sensitive bacteria quantification is achieved by indirect electrochemistry detection and immunomagnetic separation with formation of a sandwich complex [Sensor, 15, 12034-1205, 2015]. Specific and sensitive detection of bacteria has been recently demonstrated using aptamer-coated magnetic beads and antibiotic-capped gold nanoclusters [Anal. Chem., 88 (1), 820-825, 2016].

Fast detection is also obtained by using magnetic beads in combination with lyotropic liquid crystals [U.S. Pat. No. 6,171,802 B1, U.S. Pat. No. 7,745,220 B2, U.S. Pat. No. 6,411,354 B1, U.S. Pat. No. 6,570,632 B2]. The formation of an immune complex by binding of antibody coated magnetic microbeads to bacteria creates a deformation in an aligned liquid crystal (LC), whereby a detectable optical signal is generated. Lyotropic liquid crystals of a non-surfactant nature which are known as lyotropic chromonic liquid crystals are best suited for such technology, due their non-toxic nature, and therefore compatibility with biological systems. Similarly to surfactant based lyotropic liquid crystals, chromonics form a liquid crystal phase when mixed with a solvent, generally water or physiological buffers. The mechanism of aggregation does not involve the formation of micelles at a critical concentration, but the chromonic molecules stack face to face, forming polydisperse, rod-like aggregates [J. Lydon, Chromonics, in: Handbook of Liquid Crystals (Wiley-VCH, Weinheim, 1998) v. 2B, p. 981 and Current Opin. Col. Inter. Sci. 3, 458 (1998)]. The aggregation is driven by weak non covalent interactions such as π-π attraction, and the length of the aggregates depends on concentration and temperature.

Detection of pathogenic material/bacteria using chromonics requires the material to align in a specific direction (uniform planar or homeotropic) when confined in a closed cell. The alignment can be obtained using aligning materials such as polyimides. Chromonic azodyes can be readily aligned homeotropically on hydrophobic substrates with very low surface tension as disclosed in Applicant's currently pending patent application for System and Method for Detecting Pathogens on Treated and Untreated Substrates Using Liquid Crystal Chromonic Azo Dye, U.S. Patent Application Publication No. US2016/0139054 A1, published on May 19, 2016.

An exemplary prior art detection technology having a non-surfactant lyotropic chromonic liquid crystal (LCLC) cell is designated generally by the numeral 40 in FIG. 1. The cell 40 includes a pair of opposed substrates or boundary plates 42, which are sealed in a manner known in the art and which contains lyotropic liquid crystal material 44. Qualitatively, the difference between LCLC's and surfactant type lyotropic materials is that LCLC molecules, designated generally by the numeral 46 in FIG. 1, are disc-like or plank-like rather than rod-like. The polar hydrophilic parts 48 form the periphery of each molecule, while the central core 50 is relatively hydrophobic. This distinction creates a range of different ordered structures. Individual disc-like molecules may form cylindrical aggregates 54 in water 56. The direction of average molecular orientation is defined by the orientation of the normals to the planes of the plank-like or disc-like molecule and indicated by, a director 60 disposed along the longitudinal axis n of the cylindrical aggregate showing the direction of orientation. In the example depicted in FIG. 1, the long axes of the aggregates are oriented in a direction parallel to the bounding plates or substrates. However, the aggregates do not necessarily align in the same parallel direction. Such an alignment requires a special treatment of the substrates. An efficient detection of ligands is possible when a ligand-receptor complex disturbs a uniform alignment of the liquid crystal in an LC cell.

Another exemplary prior art non-surfactant lyotropic liquid crystal cell with homeotropic alignment used for the detection and amplification of ligands is shown schematically in FIG. 2 and designated generally by the numeral 70. The cell 70 includes a pair of opposed substrates or boundary plates 72, which are sealed in a well-known manner. The cell contains a lyotropic chromonic liquid crystal material 74 in water 76. The difference between material 74 and the prior art chromonic material 44 of FIG. 1 lies in the preferential alignment of chromonic material 74. On a variety of substrates, this alignment is homeotropic, meaning the long axes of the aggregates (one of which is shown at n) are oriented in a direction perpendicular to the bounding plates. Director 78 shows the direction of orientation. An efficient detection of ligands is possible when the ligand-receptor complex disturbs the homeotropic alignment of the liquid crystal in the liquid crystal cell.

The efficiency of this type of detection depends not only on the formation of an immune complex by ligand-receptor binding, but requires the formation of ligand-receptor clusters large enough to create a deformation of the aligned LC creating an optical signal intensity which is higher than the background signal intensity generated by the receptor-receptor pairs' spontaneous aggregation.

To be able to improve the technology further by eliminating the background signal and increasing detection sensitivity a need exists for an alternative simplified capture and amplification mechanism which maximizes the effect of ligand-receptor pair by creating a deformation in the aligned LC and minimizing the effect of spontaneously forming receptor-receptor pairs.

SUMMARY OF THE INVENTION

In order to achieve above-referenced technological advances, the present invention provides a system and method for the fast detection of ligands comprising a two-bead method and a homeotropically aligned chromonic liquid crystal system.

In one embodiment the present invention provides a system and method for the fast detection of ligands comprising a two-receptor method, wherein the receptors are in the form of beads and the beads and the ligand form a bead-ligand-bead "sandwich" bio-species.

In another embodiment the present invention provides a system for the detection of pathogens comprising a "sandwich" biospecies and an amplification mechanism.

In yet another embodiment, a system and method for the fast detection of ligands are provided comprising a homeotropic aligned liquid crystal wherein an amplified signal is created by the distortion of the alignment in the presence of a "sandwich" bio-species.

In an embodiment, the present invention provides a system and method for the fast detection of ligands comprising a two-bead method, wherein the beads are coated with receptors for linking to specific antigens.

In another embodiment, the present invention provides a system and method for the fast detection of ligands comprising a two-bead method, wherein the beads are coated with receptors for linking to specific antigens; one type of coated beads being magnetic and 3 microns in size or smaller, and the other type of coated beads being non-magnetic, polymeric with a size of 3 microns or larger.

In yet another embodiment, the present invention provides a system and method for the fast detection of ligands comprising a two-bead method wherein the method is based on a two-step protocol: the first step requiring isolation and concentration of ligands using magnetic beads 3 microns in size or smaller coated with receptors for linking to specific antigens, and the second step requiring binding of captured ligands to non-magnetic, polymeric beads in size 3 microns or larger, and coated with receptors for linking to specific antigens.

In a further embodiment, the present invention provides a system and method for the fast detection of ligands comprising a two-bead method and amplification mechanism including a homeotropically aligned lyotropic chromonic liquid crystal, wherein the liquid crystal is sandwiched between a pair of substrates.

In another embodiment, the present invention provides a system and method for the fast detection of ligands comprising a two-bead method and amplification mechanism comprising a homeotropically aligned lyotropic chromonic liquid crystal, wherein the liquid crystal material is a chromonic azodye.

In still another embodiment, the present invention provides homeotropic alignment of a liquid crystal, wherein the chromonic azodye is mixed with a "sandwich" biospecies which is then disposed between the substrates and observed to determine whether the biospecies distorts alignment of the liquid crystal material.

These and other features, aspects and advantages of the present invention will be apparent from the accompanying detailed disruption of the invention, which, taken with the appended drawings, discloses the embodiment thereof.

BRIEF DESCRIPTION OF THE DRAWINGS

Referring now to the attached drawings which form a part of this original disclosure:

FIG. 8.A is a graphical representation of an events count comparison between positive and control samples in example 2 (A); and FIG. 8.B is a graphical representation of an events count comparison between positive and control samples in example 3 (B).

DETAILED DESCRIPTION OF THE INVENTION

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Figure 1:
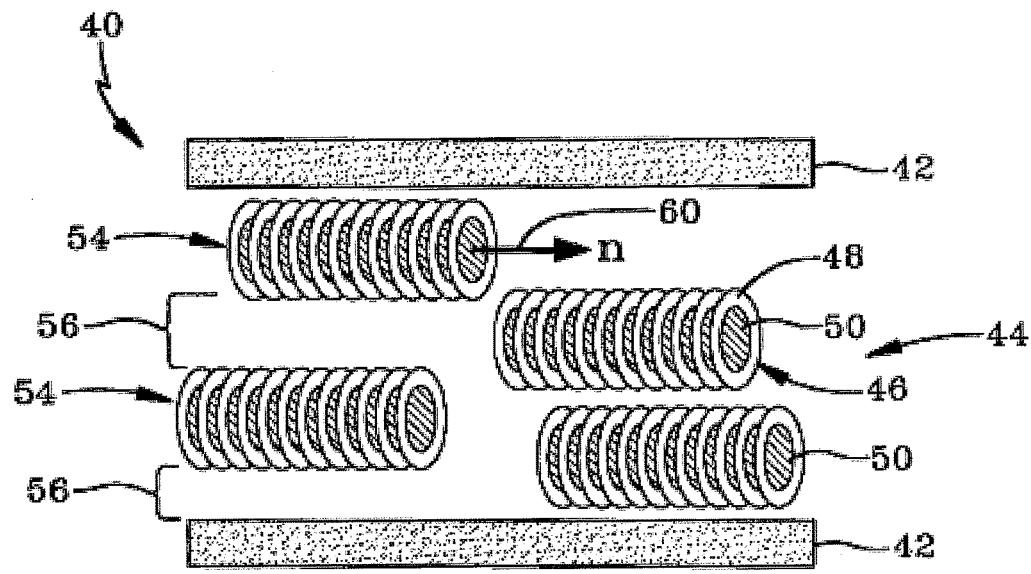
FIG. 1 is a schematic cross-sectional view of a prior art lyotropic chromonic liquid crystal cell with planar alignment.
Figure 2:
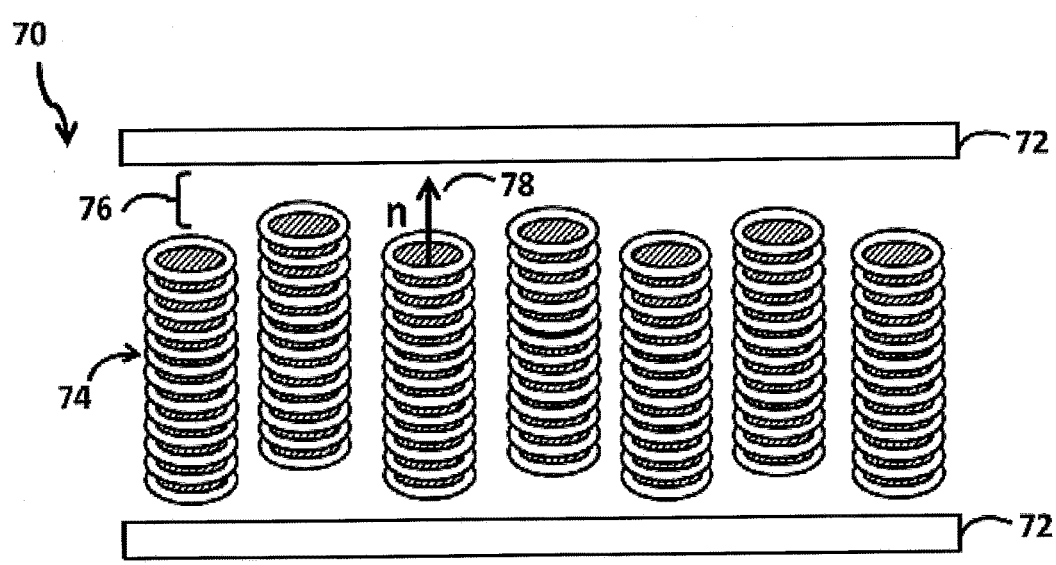
FIG. 2 is a schematic cross-sectional view of a prior art lyotropic chromonic liquid crystal cell with homeotropic alignment.
Figure 3:
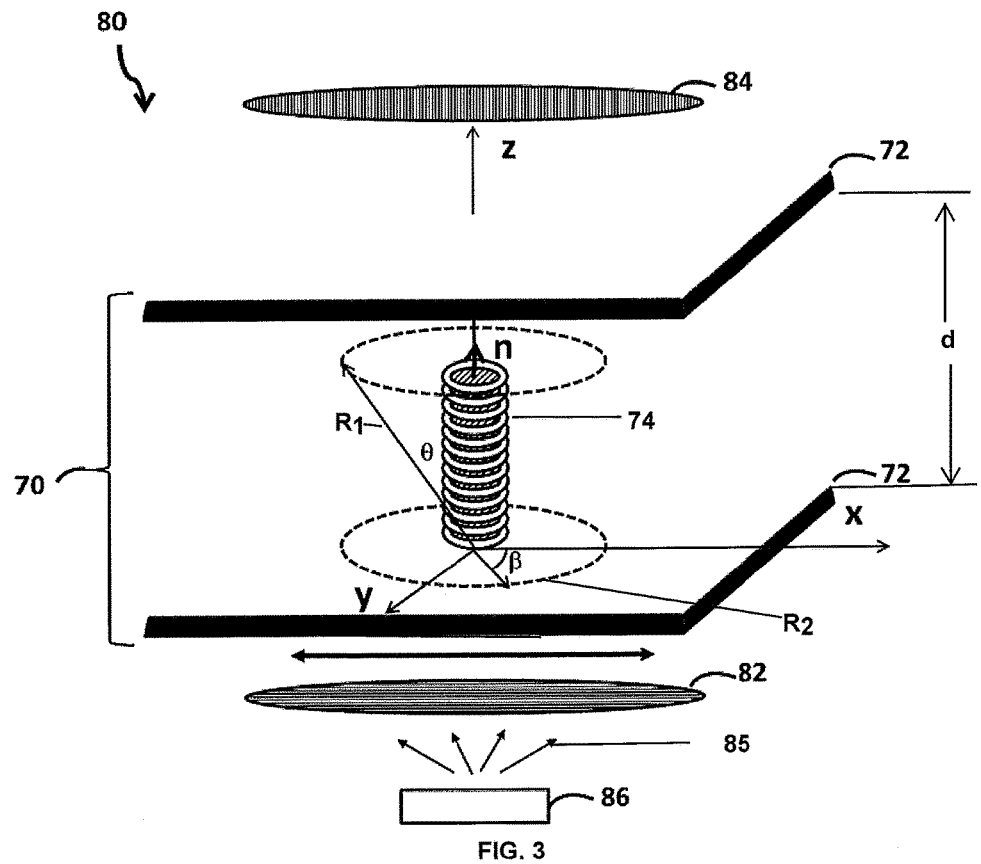
FIG. 3 is a schematic drawing of a lyotropic chromonic liquid crystal cell coupled with a light source and polarizers.

Referring to FIG. 3, a detection device in accordance with the present invention is designated generally by the numeral 80 and includes a cell 70 adapted to receive a test sample of material positioned intermediate two crossed polarizers 82, 84 spaced apart at a preselected spacing or distance d. An unpolarized light beam 85 from a light source 86 impinges on polarizer 82 placed between the light source 86 and the cell. The polarizer makes the impinging light linearly polarized, which, in turn, impinges normally on the cell in the direction of an axis Z.

In a homeotropically aligned cell, ideally, no direction is preferred in the x-y plane; the system is rotationally symmetric as discussed earlier, an exemplary lyotropic liquid crystal (LLC) 74 having a longitudinal axis n is shown in perpendicular alignment to the substrate 72. If a deformation is introduced, such as a receptor-ligand complex, the aggregates deviate a certain acute angle from the perpendicular direction around the disturbance. The incident polarized light entering the cell with local anisotropic distortion, splits into ordinary and extraordinary light waves having mutually orthogonal polarizations and travelling at different speeds. Because the two components travel at different velocities, the waves are out of phase. When the rays are recombined as they exit the liquid crystal cell, the phase difference results in a change in the polarization state. Thus the linear polarized light becomes elliptically polarized (as shown graphically by $R_1$ at an angle θ to the Z axis and by $R_2$ at an angle β to the X axis), and a light component passes through the second polarizer) 84 to a photo detector (not shown).

Figure 4:
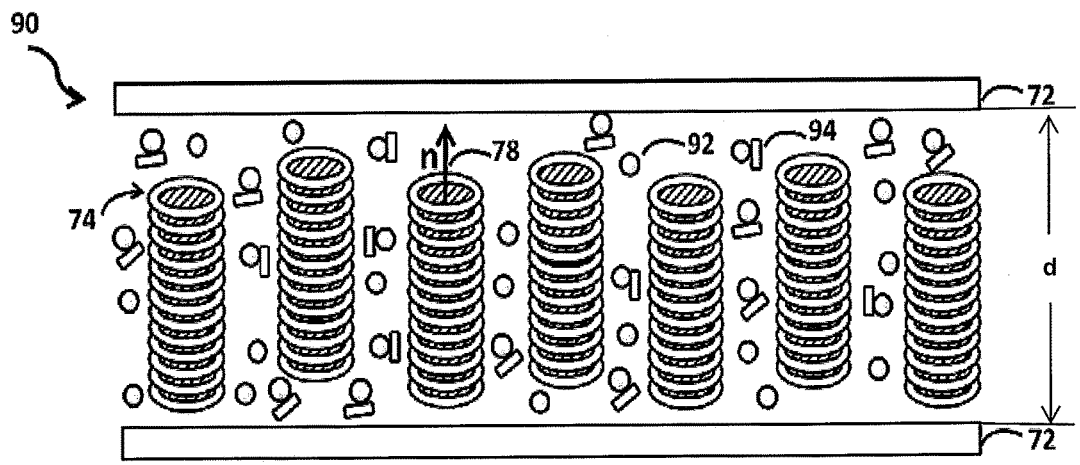
FIG. 4 is a schematic view of a lyotropic chromonic liquid crystal cell without a detected material.
Figure 5:
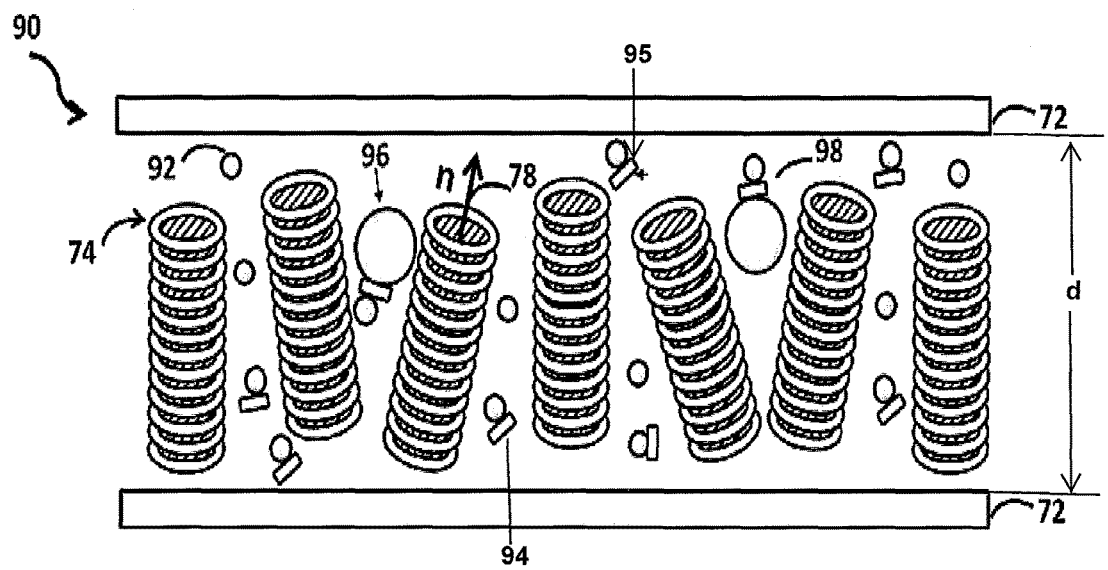
FIG. 5 is a schematic view of a lyotropic chromonic liquid crystal cell with a detected material.

An exemplary non-surfactant lyotropic liquid crystal cell with hometropic alignment used for the detection and amplification of ligands in a material test sample is shown schematically in FIG. 4 and designated generally by the numeral 90. The cell includes a pair of opposed substrates 72 positioned therein spaced apart at a preselected distance d and a lyotropic chromonic liquid crystal material 74 oriented in such a way that the director n as described above is everywhere perpendicular to the cell substrates. In the presence of small disturbance created, for example, by one of a plurality of first receptors 92, such as magnetic particles or beads each having a size of 3 microns or less and being coated with an antibody or DNA aptamer structured and arranged to bind to a ligand, or by a complex formed by receptor 92 binding to a ligand 94, such as a microbe, or by receptor 92's spontaneous aggregation with other receptors 92, no disruption of this alignment is created. However, as seen in FIG. 5, in the presence of a plurality of second secondary larger receptors 96, such as polymeric particles or beads each having a size of 3 microns or greater and being coated with an antibody or DNA aptamer structured and arranged to bind to a ligand, a sufficiently large receptor-ligand-receptor layered biospecies 98 is formed with the ligand positioned intermediate each of the receptors in a "sandwiched" structure or configuration. The layered or sandwiched biospecies 98 is of sufficient size to distort the liquid crystal orientation locally; whereby light is transmitted through the liquid crystal material producing a detectable optic signal. The signal indicates the presence of a pathogenic material, microbe, bacteria or other substance of interest.

Thus, in one preferred embodiment of the present invention, a sufficiently large "sandwich" biospecies 98 is formed following a two-step protocol, wherein in the first step, a ligand 94, such as a microbe, is permitted to bind to a small receptor 92, such as, for example, 3 micron magnetic beads or smaller coated with specific antibody or DNA aptamer whereby a first or small receptor-ligand complex 95 is formed, which is sufficiently small so as not to disturb the homeotropically aligned liquid crystal material. In the second step, a large receptor 96, such as one of a plurality of polymeric beads of a size 3 microns or larger coated with a specific antibody or DNA aptamer and contained within the liquid crystal material in the cell, is permitted to bind to the ligand-small receptor complex 95 whereby the layered or sandwiched biospecies 98 is formed.

The small receptor 92 must be capable of binding to a desired ligand 94 to form a small receptor-ligand complex 95 such that, upon formation of said small receptor-ligand complex, no detectable optical signal is produced. The large receptor 96 must be capable of binding to the small receptor-ligand complex such that, upon formation of a small receptor-ligand-large receptor "sandwich" complex or biospecies 98, a detectable optical signal is produced. The specific antibodies or DNA aptamers may be attached to the beads in any manner known to art, including chemical attachment and physical attachment.

In an embodiment, a sufficiently large "sandwich" biospecies 98 is mixed with chromonic liquid crystal material 74 and the mixture is injected with either positive or negative pressure between two substrates 72 assembled and sealed in a well-known manner. By way of example and not of limitation, the substrates may be glass coated with hydrophobic, low surface energy materials such as but not limited to polyimides, spray acrylics, super-hydrophobic coating or uncoated plastics such as a cyclic olefin copolymer (COC) or a cyclo-olefin polymer (COP) plastic. In one embodiment, the substrates are soda lime glass coated with 7511 polyimide.

In yet another embodiment the assembled cell is inserted in a detection device, consisting of a light source, two linear polarizers in crossed position and a photo detector. The liquid crystal cell is positioned inbetween the two polarizers. The large "sandwich" biospecies 98 induces a distortion of the aligned liquid crystal generating optically detectable birefringence, which is shown in a photomicrograph of a cell as seen under a microscope in FIG. 6. Furthermore, as noted above with respect to the embodiments of FIGS. 4 and 5, small receptor pairs and small receptor-ligand complexes do not induce any distortion of the aligned liquid crystal, thereby minimizing the effect of the background signal.

Procedure

The following examples describe the mechanism of detection of *E. coli* O157 by a two-step receptor-ligand interaction and by a liquid crystal amplification mechanism in accordance with the instant invention. The examples are intended for illustrative purpose only, and should not be considered as limiting the scope of the present invention in any manner. Any modifications fall within the scope of the claimed invention, and thus the selection of specific receptor, ligand, aligning coating and substrate, aligning direction (uniformly planar or homeotropic) or liquid crystal can be determined without departing form the spirit of the invention herein disclosed and described.

Figure 6:
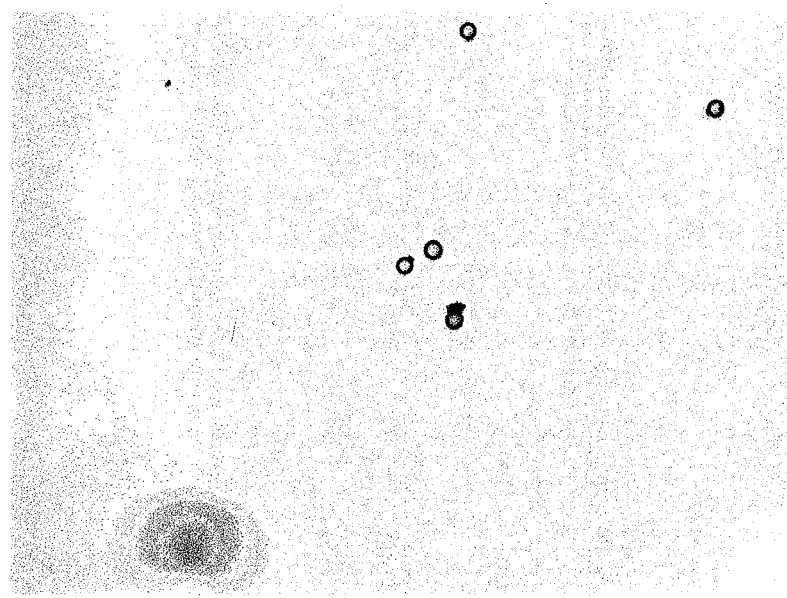
FIG. 6. is a photomicrograph of a sandwich biospecies observed under optical microscope with uncrossed polarizers.

An exemplary ligand detection system was created by inserting antibody-coated beads of different type and size into a chromonic azo dye liquid crystal. In the presence of ligand-receptor interaction, the formation of a large sandwich complex creates a deformation of the liquid crystal alignment that can be easily detected (FIG. 6). The chromonic liquid crystal was formed when azo dye Sunset Yellow (Spectrum) was dissolved in saline buffer to form a 35.6% solution. The liquid crystal solution remained nematic at room temperature when diluted to 30%.

The homeotropic liquid crystal orientation was obtained by print coating and curing 7511 polyimide on soda lime glass, and the substrates assembled thereafter to create an assay chamber with thickness controlled by 20 micron glass spacers. A nematic buffer solution of chromonic azo dye mixed with beads was injected in the assay chamber at room temperature using positive pressure. After relaxation of a transient stripe texture due to flow-induced planar alignment, the LCLC spontaneously orients homeotropically. Commercially available 1 micron magnetic beads with anti-*E. coli* antibody coating were obtained (Lifetech *E. coli* O157 MAX). A stock solution of assay positive beads ($5 \times 10^6$/100 microliter) was created in storage buffer.

Commercially available 1 micron magnetic beads with streptavidin coating such as those produced by Invitrogen) were coated with IgG antibody and used as negative control. A stock solution of assay negative beads ($5 \times 10^6$/100 microliter) was created in storage buffer.

A commercially available anti-*Ecoli* O157 antibody (BacTrace Affinity Purified Antibody Goat anti *E. coli* O157:H7, KPL) was obtained and used at the concentration of 1 mg/ml.

Commercially available 10 micron sulfate latex beads available from Fisher were coated with the anti-*Ecoli* O157 antibody by physical absorption protocol. A stock solution of assay positive beads ($2 \times 10^6$/100 microliter) was created in storage buffer.

Commercially available 10 micron polystyrene beads were obtained (Polysciences). The polymeric beads were coated with the anti-*Ecoli* O157 antibody by physical absorption protocol, and a stock solution of assay positive beads ($2 \times 10^6$/100 microliter) was created in storage buffer.

A Culture of *E. coli* was grown to mid log growth phase in tryptic soy broth and the optical density of the suspension at 600 nm was measured and the bacteria concentration extrapolated from a growth curve (optical density at 600 nm versus colony-forming units (CFUs)). $7 \times 10^4$/ml and $3.5 \times 10^4$/ml stock bacteria solutions were prepared using sterile phosphate buffered saline (PBS).

Example 1

600 microliter of $7 \times 10^4$/ml *E. coli* stock solution are incubated for 10 minutes with 100 microliter of 1 micron positive beads. The beads are collected with a magnetic block, washed on the magnet with PBS, re-suspended in 50 microliter PBS and incubated for 5 minutes at room temperature with 100 microliter of 10 micron sulfate latex positive beads. The beads are collected with a magnetic block, washed on magnet with PBS and re-suspended in 15 microliter of PBS.

10 microliter of beads are mixed with 56 microliter of 35.6% stock saline buffer solution of liquid crystal at room temperature. A 60 microliter fraction of the mixture was introduced into the glass assay chamber described above.

As a control test, 600 microliter of $7 \times 10^4$/ml *E. coli* stock solution are incubated for 10 minutes at room temperature with 100 microliter of 1 micron negative beads.

The beads are collected with a magnetic block, washed on the magnet with PBS, re-suspended in 50 microliter PBS and incubated for 5 minutes at room temperature with 100 microliter of 10 micron sulfate latex positive beads. These beads are collected with a magnetic block, washed on magnet with PBS and re-suspended in 15 microliter of PBS. 10 microliter of beads are mixed with 56 microliter of 35.6% stock saline buffer solution of liquid crystal at room temperature. A 60 microliter fraction of the mixture was introduced into the glass assay chamber described above.

Each mixture was evaluated inserting the assay chamber in the detection device and quantifying the number of light transmissive zones (number of events).

Figure 7:
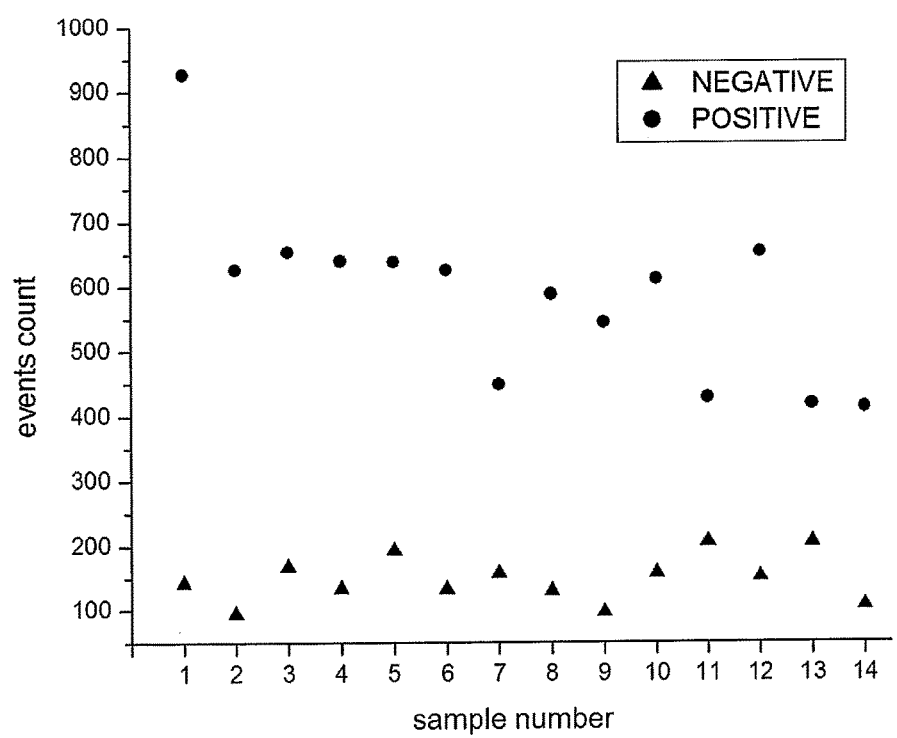
FIG. 7. is a graphical representation of an events count comparison between positive and control samples in example 1.

FIG. 6 shows the sandwich complex observed using an optical microscope with uncrossed polarizers at 10X objective magnification, and FIG. 7 shows that formation of sandwich bio-species translates in an increase of the number of events count in all fourteen samples compared to the control samples.

Example 2

600 microliter of $7 \times 10^4$/ml *E. coli* stock solution are incubated for 10 minutes with 100 microliter of 1 micron positive beads. The beads are collected with a magnetic block, washed on the magnet with PBS, re-suspended in 50 microliter PBS and incubated for 10 minutes at room temperature with 100 microliter of 10 micron polystyrene positive beads. The beads are collected with a magnetic block, washed on magnet with PBS and re-suspended in 15 microliter of PBS.

10 microliter of beads are mixed with 56 microliter of 35.6% stock saline buffer solution of liquid crystal at room temperature. A 60 microliter fraction of the mixture was introduced into the glass assay chamber described above.

As a control test, 600 microliter of $7 \times 10^4$/ml *E. coli* stock solution are incubated for 10 minutes at room temperature with 100 microliter of 1 micron negative beads.

The beads are collected with a magnetic block, washed on the magnet with PBS, re-suspended in 50 microliter PBS and incubated for 10 minutes at room temperature with 100 microliter of 10 micron polystyrene positive beads. These beads are collected with a magnetic block, washed on magnet with PBS and re-suspended in 15 microliter of PBS. 10 microliter of beads are mixed with 56 microliter of 35.6% stock saline buffer solution of liquid crystal at room temperature. A 60 microliter fraction of the mixture was introduced into the glass assay chamber described above.

FIG. 8.A shows that formation of sandwich bio-species translates in an increase of the number of events count in all 10 samples compared to the control samples.

Example 3

600 microliter of $3.5 \times 10^4$/ml *E. coli* stock solution are incubated for 10 minutes with 100 microliter of 1 micron positive beads. The beads are collected with a magnetic block, washed on the magnet with PBS, re-suspended in 50 microliter PBS and incubated for 10 minutes at room temperature with 100 microliter of 10 micron polystyrene positive beads. The beads are collected with a magnetic block, washed on magnet with PBS and re-suspended in 15 microliter of PBS.

10 microliter of beads are mixed with 56 microliter of 35.6% stock saline buffer solution of liquid crystal at room temperature. A 60 microliter fraction of the mixture was introduced into the glass assay chamber described above.

As a control test, 600 microliter of $3.5 \times 10^4$/ml *E. coli* stock solution are incubated for 10 minutes at room temperature with 100 microliter of 1 micron negative beads.

The beads are collected with a magnetic block, washed on the magnet with PBS, re-suspended in 50 microliter PBS and incubated for 10 minutes at room temperature with 100 microliter of 10 micron polystyrene positive beads. These beads are collected with a magnetic block, washed on magnet with PBS and re-suspended in 15 microliter of PBS. 10 microliter of beads are mixed with 56 microliter of 35.6% stock saline buffer solution of liquid crystal at room temperature. A 60 microliter fraction of the mixture was introduced into the glass assay chamber described above.

FIG. 8.B shows that formation of sandwich bio-species translates in an increase of the number of events count in all 10 samples compared to the control samples.

Changes may be made in the above methods and systems without departing from the scope hereof. It should be noted that the matter contained in the above description and/or shown in the accompanying figures should be interpreted as illustrative and not in a limiting sense. The following claims are intended to cover all generic and specific features described herein, as well as all statements of the scope of the present systems and methods, which, as a matter of language, might be said to fall there between.

What is claimed is:

1. An apparatus for the rapid detection of ligands in a material test sample, the apparatus comprising:
   a source of unpolarized light;
   a pair of crossed polarizers spaced apart at a preselected distance and adapted to receive the unpolarized light from the light source;

a cell adapted to receive the test sample positioned intermediate the spaced apart crossed polarizers, the cell including a pair of opposed substrates positioned therein and spaced apart at a preselected distance;

a non-surfactant lyotropic chromonic liquid crystal material (LCLC) contained in the cell and homeotropically aligned with respect to each of the opposed substrates;

a plurality of first or small receptors contained within the liquid crystal material, each of the plurality of first receptors having a size of 3 microns or less and being coated with an antibody or a DNA aptamer structured and arranged to bind to a ligand whereby at least one first or small receptor-ligand complex is formed which is structured and arranged to be sufficiently small so as to not to deform the homeotropical alignment of the lyotropic liquid crystal;

a plurality of second or large receptors contained within the liquid crystal material, each of the plurality of second receptors having a size of 3 microns or greater and being coated with an antibody or a DNA aptamer structured and arranged to bind to the at least one first or small receptor ligand complex, whereby a small receptor-ligand-large receptor sandwich-like complex or biospecies is formed, the sandwich-like complex being structured and arranged to be sufficiently large so as to deform the homeotropic alignment of the liquid whereby a detectable optical signal is produced; and a photo detector adapted to receive the detectable optical signal.

2. The detection apparatus of claim 1 wherein the lyotropic chromonic liquid crystal material comprises a plurality of disc-like molecules structured and arranged to form a plurality of cylindrical aggregates, each of the aggregates having a longitudinal axis or director being in undeformed homeotropic alignment within the cell in an orientation direction which is perpendicular to the opposed substrates.

3. The detection apparatus of claim 2 wherein the orientation direction of the longitudinal axes or directors of at least a portion of the cylindrical aggregates deviates from perpendicular to the opposed substrates to an acute angel with respect thereto in response to a deformation of the alignment by a sandwich-like complex.

4. The apparatus of claim 1 wherein each of the plurality of small receptors comprises a magnetic bead.

5. The apparatus of claim 1 wherein each of the plurality of large receptors comprises a non-magnetic polymeric bead.

6. The apparatus of claim 1 wherein each of the pair of opposed substrates are comprised of glass.

7. The apparatus of claim 6 each of the substrates are coated with a hydrophobic, low energy material.

8. The apparatus of claim 7 wherein the hydrophobic, low energy material comprises a polyimide, an acrylic, a coated or uncoated plastic, a cyclic olefin copolymer (COC) plastic or a cyclo-olefin polymer (COP) plastic.

9. The apparatus of claim 1 wherein each of the pair of opposed substrates comprises soda lime glass coated with 7511 polyimide.

* * * * *